(12) United States Patent
Kawagishi et al.

(10) Patent No.: US 10,290,096 B2
(45) Date of Patent: May 14, 2019

(54) DIAGNOSIS SUPPORT APPARATUS, INFORMATION PROCESSING METHOD, AND STORAGE MEDIUM

(71) Applicant: CANON KABUSHIKI KAISHA, Tokyo (JP)

(72) Inventors: Masami Kawagishi, Kyoto (JP); Koji Sakai, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 134 days.

(21) Appl. No.: 15/097,422

(22) Filed: Apr. 13, 2016

(65) Prior Publication Data

US 2016/0335764 A1    Nov. 17, 2016

(30) Foreign Application Priority Data

May 14, 2015    (JP) ................. 2015-099513

(51) Int. Cl.
| G06K 9/46 | (2006.01) |
| G06T 7/00 | (2017.01) |
| G06K 9/62 | (2006.01) |
| G06F 19/00 | (2018.01) |
| G16H 50/20 | (2018.01) |

(52) U.S. Cl.
CPC .......... *G06T 7/0012* (2013.01); *G06F 19/321* (2013.01); *G06F 19/325* (2013.01); *G06K 9/6254* (2013.01); *G06K 9/6278* (2013.01); *G06K 9/6296* (2013.01); *G16H 50/20* (2018.01); *G06K 2209/05* (2013.01); *G06T 2207/10072* (2013.01); *G06T 2207/10116* (2013.01);

(Continued)

(58) Field of Classification Search
CPC ............ G06K 2209/05; G06K 9/6254; G06K 9/6278; G06K 9/6296; G06T 7/0012
See application file for complete search history.

(56) References Cited

U.S. PATENT DOCUMENTS

| 7,965,907 B2 | 6/2011 | Takekoshi ..................... 382/305 |
| 2002/0062075 A1* | 5/2002 | Takeo .................. G06T 7/0012 |
| | | 600/407 |

(Continued)

FOREIGN PATENT DOCUMENTS

| JP | H04-338827 | 11/1992 |
| JP | 2010-200840 | 9/2010 |

(Continued)

OTHER PUBLICATIONS

Machine Translated JP2004173910.*

*Primary Examiner* — Sing-Wai Wu
(74) *Attorney, Agent, or Firm* — Venable LLP (57) ABSTRACT

A diagnosis support apparatus provides information for supporting medical diagnosis. The diagnosis support apparatus includes: a selection unit configured to select reference information as a clue for medical diagnosis from reference information candidates generated by using medical information; an obtaining unit configured to obtain an image feature corresponding to the reference information from a medical image; a specifying unit configured to specify a partial region of the medical image based on the reference information and the image feature; and a display control unit configured to control display of the medical image based on the selected reference information and the partial region.

19 Claims, 8 Drawing Sheets

(52) U.S. Cl.
CPC ............ *G06T 2207/20081* (2013.01); *G06T 2207/30096* (2013.01)

(56) References Cited

U.S. PATENT DOCUMENTS

| | | | |
|---|---|---|---|
| 2010/0332441 A1 | 12/2010 | Kawagishi et al. | 706/52 |
| 2011/0161278 A1 | 6/2011 | Kawagishi | 706/52 |
| 2011/0199390 A1 | 8/2011 | Iizuka et al. | 345/629 |
| 2011/0213748 A1 | 9/2011 | Kawagishi et al. | 706/52 |
| 2012/0136882 A1 | 5/2012 | Kawagishi et al. | 707/758 |
| 2012/0254101 A1 | 10/2012 | Kawagishi | 706/52 |
| 2013/0212056 A1 | 8/2013 | Kawagishi | 706/46 |
| 2014/0140593 A1* | 5/2014 | Park | G06T 7/0012 382/128 |
| 2014/0195472 A1 | 7/2014 | Kawagishi | 706/46 |

FOREIGN PATENT DOCUMENTS

| | | |
|---|---|---|
| JP | 2011-131022 | 7/2011 |
| JP | 2012-245395 | 12/2012 |

\* cited by examiner

| j | I$_j$(ITEM) | jk | S$_{jk}$(STATE) |
|---|---|---|---|
| 1 | SHAPE | 11 | SPHERE |
| | | 12 | LOBULAR |
| | | 13 | IRREGULAR |
| 2 | NOTCH | 21 | STRONG |
| | | 22 | INTERMEDIATE |
| | | 23 | WEAK |
| | | 24 | ABSENT |
| 3 | SERRATED PERIPHERY | 31 | STRONG |
| | | 32 | INTERMEDIATE |
| | | 33 | WEAK |
| | | 34 | ABSENT |
| ... | | | |
| l | INVOLVEMENT (BRONCHUS) | l1 | PRESENT |
| | | l2 | SUSPECTED |
| | | l3 | ABSENT |
| ... | | | |
| m | CEA | m1 | NORMAL VALUE |
| | | m2 | ABNORMAL VALUE |
| ... | | | |
| n | HISTORY | n1 | PRESENT |
| | | n2 | ABSENT |

FIG. 6A

SERRATED PERIPHERY: STRONG

FIG. 6B

CALCIFICATION: PRESENT

FIG. 6C

NOTCH: STRONG

FIG. 6D

CEA: ABNORMAL VALUE

EXAMPLE OF SURROUNDING
REGION WITH RECTANGLE

FIG. 8B

EXAMPLE OF ADDING ARROW TO
PORTION IN VICINITY OF REGION

DIAGNOSIS SUPPORT APPARATUS, INFORMATION PROCESSING METHOD, AND STORAGE MEDIUM

BACKGROUND OF THE INVENTION

Field of the Invention

The present invention relates to a diagnosis support apparatus, an information processing method, and a storage medium.

Description of the Related Art

In the medical field, doctors perform the image diagnosis of performing diagnosis by interpreting medical images obtained by imaging apparatuses such as an X-ray CT (Computed Tomography) apparatus and an MRI (Magnetic Resonance Imaging) apparatus. When performing image diagnosis, in accordance with a radiogram interpretation request from a primary doctor, a doctor who interprets medical images identifies the symptom of a lesion depicted in an image by comprehensively determining the findings (to be referred to as "imaging findings" hereinafter) obtained from images and various types of measurement values. The doctor who interprets medical images then compiles the process of reaching the diagnosis into a radiogram interpretation report to the primary doctor as the request source by using image findings and measurement values.

For the purpose of supporting such radiogram interpretation, there has been developed a medical diagnosis support system. For example, Japanese Patent Laid-Open No. 2010-200840 has disclosed a technique of identifying information, of input information, which influences an inference result based on the input information, and presenting the identified information to the user. The technique disclosed in Japanese Patent Laid-Open No. 2010-200840 can present information as a clue for diagnosis (to be referred to as reference information hereinafter) to the user.

In addition, Japanese Patent Laid-Open No. 4-338827 has disclosed a technique of deciding video information corresponding to an inference result from a database as reference information of an inference result based on input information and presenting the information to the user. The technique disclosed in Japanese Patent Laid-Open No. 4-338827 can present reference information as visual information.

However, the technique disclosed in Japanese Patent Laid-Open No. 2010-200840 is limited to the presentation of reference information. If reference information is information (imaging finding) associated with an image, since the information does not indicate any specific portion on the image which corresponds to the imaging finding, the user needs to search for the imaging finding by himself/herself.

Although the technique disclosed in Japanese Patent Laid-Open No. 4-338827 presents visual information, the presented information is predetermined video information. For this reason, the image browsed by the user sometimes does not correspond to the situation.

The present invention has been made in consideration of the above problem and provides a diagnosis support apparatus which can reduce time and effort taken by the user to comprehend reference information by presenting the reference information on an image.

SUMMARY OF THE INVENTION

According to one aspect of the present invention, there is provided a diagnosis support apparatus which provides information for supporting medical diagnosis, the apparatus comprising: a selection unit configured to select reference information as a clue for medical diagnosis from reference information candidates generated by using medical information; an obtaining unit configured to obtain an image feature corresponding to the reference information from a medical image; a specifying unit configured to specify a partial region of the medical image based on the reference information and the image feature; and a display control unit configured to control display of the medical image based on the selected reference information and the partial region.

According to another aspect of the present invention, there is provided a diagnosis support apparatus which provides information for supporting medical diagnosis, the apparatus comprising: a selection unit configured to select reference information as a clue for medical diagnosis from reference information candidates generated by using medical information; an obtaining unit configured to obtain an image feature corresponding to the reference information from a medical image; and a display control unit configured to display a partial region of the medical image which is specified based on the reference information and the image feature or a portion in the vicinity of the partial region so as to emphasize the partial region or the portion in the vicinity of the partial region relative to a remaining region.

According to the present invention, it is possible to reduce time and effort taken by the user to comprehend reference information by presenting reference information on an image.

Further features of the present invention will become apparent from the following description of exemplary embodiments (with reference to the attached drawings).

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

A diagnosis support apparatus according to the first embodiment obtains a medical image as a target for medical diagnosis (radiogram interpretation) and medical information written on an electronic health record or the like, and presents information (reference information) as a clue for diagnosis on the medical image, thereby performing diagnosis support concerning the case.

Assume that in the following description, medical images, a past medical history, and tumor marker values (to be referred to as clinical information hereinafter) are obtained as input information by using a diagnosis support apparatus which presents information for supporting medical diagnosis. The following will exemplify a case in which information (reference information) as a clue for diagnosis is identified from the obtained input information, and the information is presented on a medical image. Obviously, a diagnosis target is not limited to this. Diagnosis names, imaging findings, clinical information, and the like each are an example for the description of steps for processing by the diagnosis support apparatus.

Figure 1:
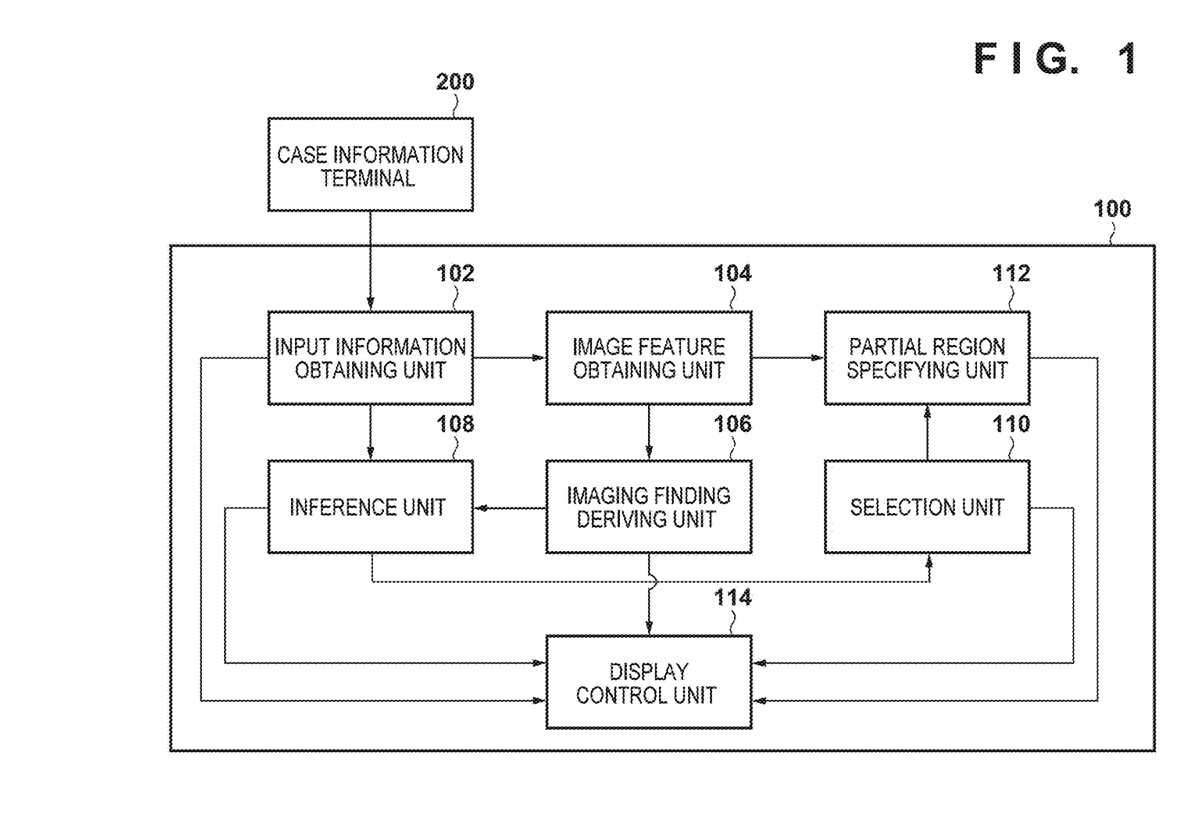
FIG. 1 is a block diagram showing an example of the functional arrangement of a diagnosis support apparatus.

FIG. 1 is a block diagram showing an example of the functional arrangement of a diagnosis support apparatus 100 according to the first embodiment. The diagnosis support apparatus 100 according to the embodiment is connected to a case information terminal 200 and can transmit/receive data to/from the case information terminal 200. The case information terminal 200 obtains medical information (medical images, electronic health record information, and the like) concerning a given case as a diagnosis target from a server (not shown). Alternatively, the case information terminal 200 can be connected to external storage devices such as an FDD, HDD, CD drive, DVD drive, MO drive, or and ZIP drive and obtain medical information from these external storage devices.

In addition, the case information terminal 200 displays these pieces of medical information on a monitor in a form that allows the user (doctor) to interpret, and can obtain coordinate information indicating a specific portion, on a medical image, in which an abnormal shadow exists based on an input from the user (doctor) via an operation unit. Alternatively, the case information terminal 200 may obtain imaging findings input by the user based on display contents. The case information terminal 200 can also obtain both coordinate information and an imaging finding. Assume that in this embodiment, the case information terminal 200 obtains only the coordinate information of an abnormal shadow input by the user, and the user inputs no imaging finding.

In accordance with a request from the user, the case information terminal 200 transmits medical information and data (coordinate information) input by the user concerning an abnormal shadow in the lung to the diagnosis support apparatus 100 via a network such as a LAN.

The diagnosis support apparatus 100 includes, as functional constituent elements, an input information obtaining unit 102, an image feature obtaining unit 104, an imaging finding deriving unit 106, an inference unit 108, a selection unit 110, a partial region specifying unit 112, and a display control unit 114.

The input information obtaining unit 102 obtains, as input information, information (such as medical information including medical image information and electronic health record information and the coordinate information of an abnormal shadow) transmitted from the case information terminal 200 to the diagnosis support apparatus 100. The input information obtaining unit 102 outputs the obtained input information to the image feature obtaining unit 104, the inference unit 108, and the display control unit 114.

The image feature obtaining unit 104 obtains an image feature (image feature amount) of a medical image as a diagnosis target by performing image processing for the medical image based on the input information obtained by the input information obtaining unit 102. The image feature obtaining unit 104 outputs the obtained image feature amount to the imaging finding deriving unit 106 and the partial region specifying unit 112.

The imaging finding deriving unit 106 derives an imaging finding based on the image feature (image feature amount) obtained by the image feature obtaining unit 104. For example, the imaging finding deriving unit 106 derives an imaging finding about a region as a diagnosis target based on a comparison result on an image feature and a threshold. The imaging finding deriving unit 106 outputs the derived imaging finding to the inference unit 108.

The inference unit 108 executes inference to obtain a diagnosis name corresponding to a diagnosis target and an inference probability corresponding to the diagnosis name based on the input information obtained by the input information obtaining unit and the imaging finding derived by the imaging finding deriving unit 106. That is, the inference unit 108 executes inference concerning an abnormal shadow in the lung as a diagnosis target based on the input information (the imaging finding and/or clinical information) obtained by the input information obtaining unit 102 and the imaging finding derived by the imaging finding deriving unit 106. The inference unit 108 can obtain inference probabilities concerning a plurality of diagnosis names as inference results. For example, in order to indicate a specific one of a plurality of diagnosis names to which an abnormal shadow on a medical image (an abnormal shadow designated by the user in this embodiment) corresponds with a high possibility, the inference unit 108 obtains a probability (inference result) at which the abnormal shadow corresponds to each of a plurality of diagnosis names. Note that in the following description, information to be used to obtain an inference result will be referred to as an evidence. In addition, the inference unit 108 obtains the influence degree of at least one reference information candidate. Specific examples of reference information candidates and a method of obtaining an influence degree will be described later. The inference unit 108 then outputs the obtained inference result and the influence degrees of reference information candidates to the selection unit 110 and the display control unit 114.

The selection unit 110 selects reference information from the reference information candidates based on the inference probabilities (inference results) and the influence degrees of the reference information candidates obtained by the inference unit 108. The selection unit 110 outputs the selected reference information to the partial region specifying unit 112 and the display control unit 114.

The partial region specifying unit 112 specifies a partial region of the medical image based on the image feature amount obtained by the image feature obtaining unit 104 and the reference information selected by the selection unit 110. Specific processing contents will be described later. The partial region specifying unit 112 outputs the specified partial region to the display control unit 114.

The display control unit 114 controls information to be displayed on a monitor (for example, a monitor attached to the case information terminal 200 or the diagnosis support apparatus 100) based on input information. The display control unit 114 can control display on the monitor so as to change, for example, the display of a partial region of a medical image specified by the partial region specifying unit 112. Specific processing contents will be described later.

At least part of each unit of the diagnosis support apparatus 100 shown in FIG. 1 may be implemented as an independent apparatus, or may be implemented as software which implements each functional constituent element. Assume that in this embodiment, each functional constituent element of each unit is implemented by software.

Figure 2:
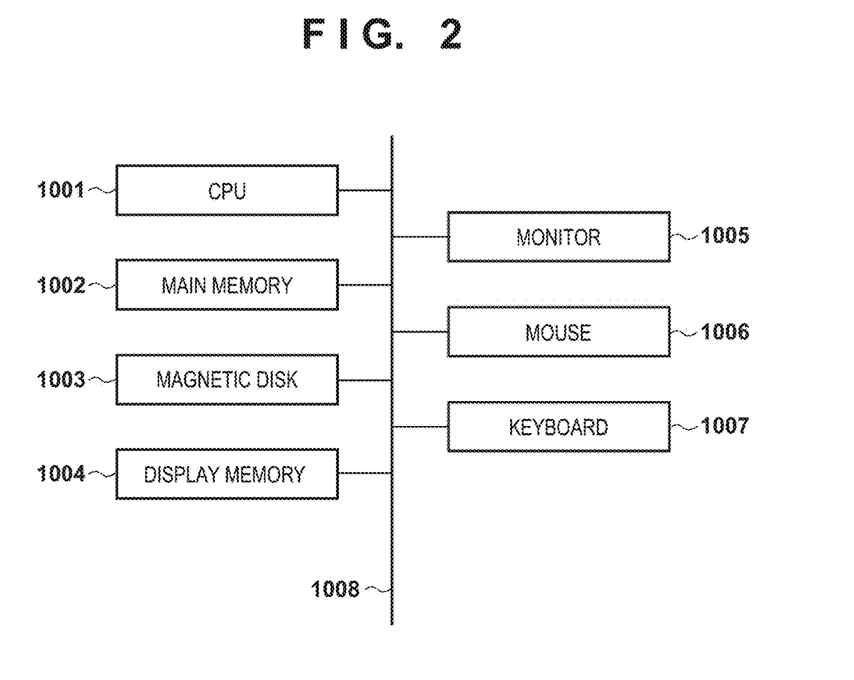
FIG. 2 is a block diagram showing an example of the hardware arrangement of the diagnosis support apparatus.

FIG. 2 is a block diagram showing an example of the hardware arrangement of the diagnosis support apparatus 100. The hardware arrangement can implement each function of each unit shown in FIG. 1 by executing software. A CPU 1001 mainly controls the operation of each constituent element. A main memory 1002 stores control programs execution by the CPU 1001, and provides a work area at the time of program executed by the CPU 1001. A magnetic disk 1003 stores programs for implementing various types of application software including an operating system (OS), device drivers for peripheral devices, and programs for performing processing (to be described later). The CPU 1001 implements the functions (software) of the diagnosis support apparatus 100 shown in FIG. 1 and processing in a flowchart (to be described later) by executing programs stored in the main memory 1002 and the magnetic disk 1003.

A display memory 1004 temporarily stores display data. A monitor 1005 (display device) is, for example, a CRT monitor or a liquid crystal monitor, and displays images, texts, and the like based on data from the display memory 1004. The user performs pointing input and inputs characters and the like by using a mouse 1006 and a keyboard 1007. The respective constituent elements described above are communicatively connected to each other via a common bus 1008.

Figure 3:
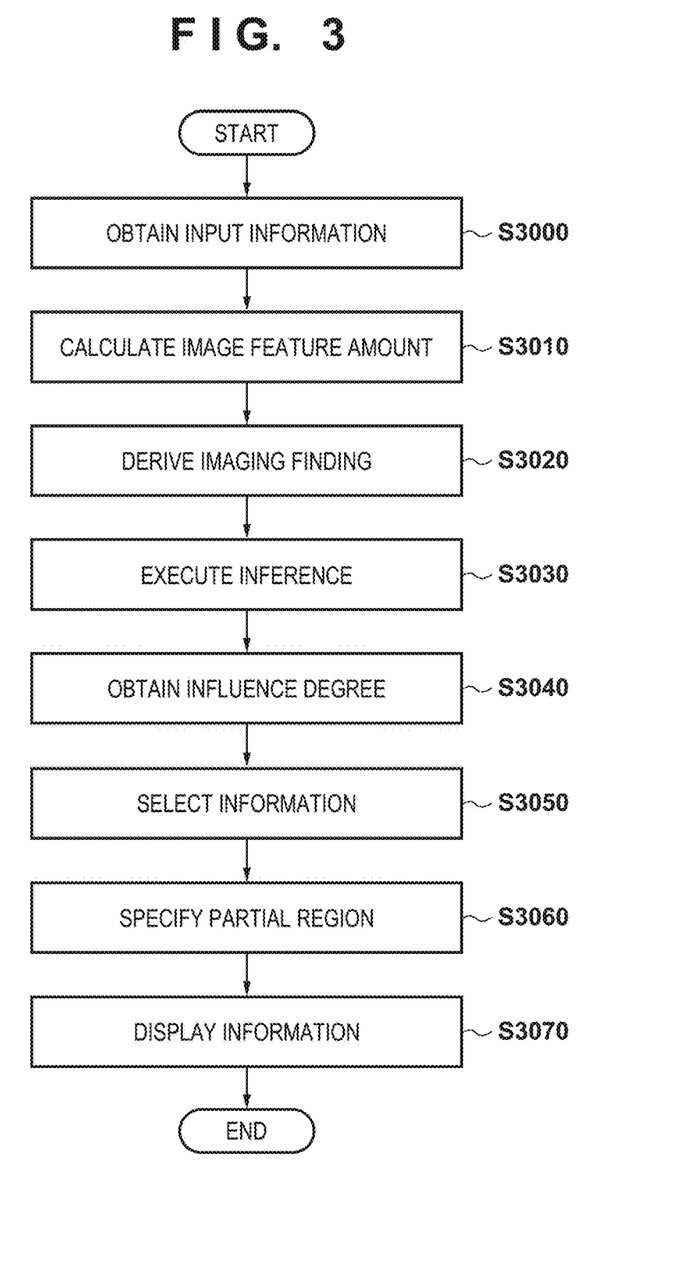
FIG. 3 is a flowchart showing an example of processing by the diagnosis support apparatus.

Processing performed by the diagnosis support apparatus 100 will be described by using the flowchart of FIG. 3. FIG. 3 is a flowchart showing a processing procedure by the diagnosis support apparatus 100 using an information processing method for providing information for supporting medical diagnosis. In this embodiment, the processing shown in FIG. 3 is implemented by causing the CPU 1001 to execute programs for implementing the functions of the respective units stored in the main memory 1002.

Figure 4:
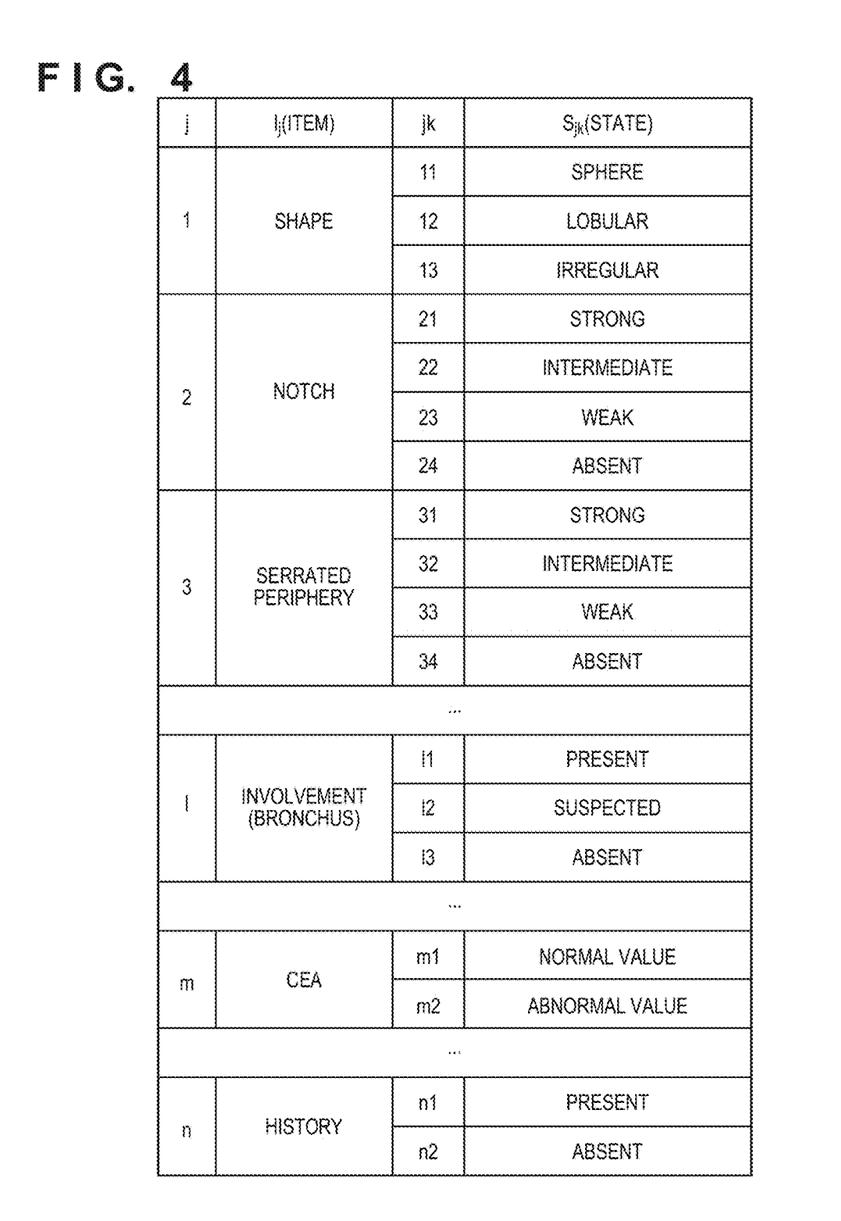
FIG. 4 is a view showing an example of imaging findings and clinical information.

In the following description, each imaging finding or clinical information name (to be referred to as an item hereinafter) associated with a case as a diagnosis target is represented by Ij (j=1 to n), and n types of items I1 to In are handled. In addition, k discrete values (to be referred to as states hereinafter) which Ij can take are written as Sjk. The range of k varies in value depending on Ij. FIG. 4 is a view showing an example of imaging findings and clinical information. In this embodiment, for example, the items shown in FIG. 4 are handled. In addition, the respective items can take states like those shown in FIG. 4. For example, "shape" of the item I1 represents the overall shape of an abnormal shadow, and takes three states, namely a state S11 "sphere", a state S12 "lobular", and a state S13 "irregular". If, for example, the item I1 takes the state S11, it indicates that the overall shape of the abnormal shadow is a sphere.

Likewise, "notch" of the item I2 represents the degree of notch in an abnormal shadow. In addition, "involvement (bronchus)" of the item I1 represents the presence/absence of the involvement of a bronchus in the abnormal shadow. Furthermore, "CEA" of Im indicates whether the value of CEA as a type of tumor marker falls within the range of values regarded as normal values. Moreover, "history" of In represents whether there is a history of a disease in the past. Note that suffixes l and m of Il and Im described above respectively indicate natural numbers between 1 and n.

In the following description, a set including, as elements, pairs of Ij and Sjk (to be written as Ij: Sjk or Ij "item name": Sjk "state name" hereinafter) is written as E. Assume however that a plurality of states Sjk corresponding to a given item Ij do not simultaneously exist in one set E. That is, one item can take only one state. For example, if states (discrete values) which the item I1 "shape" can take are S11, S12, and S13, and states (discrete values) which the item I2 "notch" can take are S21, S22, S23, and S24, E={I1: S11, S2: S21} indicates the states of "Shape" and "notch", and can take both the states. On the other hand, E={I1: S11, I1: S12} indicates the two different states ("spherical" and "lobular") of one item ("shape"), and cannot take both the states. This is because one item takes only one state.

In addition, in the following description, a diagnosis name is written by using the symbol "D". In this embodiment, diagnosis names take three values, namely primary lung cancer, lung cancer metastasis, and others, respectively written as D1, D2, and D3. In addition, the inference probability of a diagnosis name Dd (d=1, 2, 3) when the set E is input to the inference unit 108 is written as P(Dd|E). In addition, the influence degree of E on the diagnosis name Dd is written as I(Dd|E).

In this case, a set including, as elements, all items handled in this embodiment is written as Na (that is, Na={I1, I2, . . . , In}). A set including, as elements, items included in evidences (information used to obtain an inference result) is written as Nf, and a set including, as elements, pairs of the respective items of Nf and their states is written as Ef. A set including, as elements, items of Na which do not belong to Nf is written as Nv (that is, Nv=Na−Nf). Note that Nv is not based on actually obtained information unlike Nf, and hence any items belonging to Nv have no defined states. In this case, a set including, as elements, pairs of the respective items of Nv and virtually assigned states is written as Ev. Nv and/or Ev will be referred to as non-input information. That is, non-input information indicates items, other than input information, (that is, information other than input or obtained medical information) of all the items to be handled. The non-input information Ev is not uniquely determined, unlike Ef, because states are virtually assigned as described above. Alternatively, no states may be assigned to items of Ev. If no states are assigned to items, the items are handled as empty elements.

If, for example, Nv={Im, In}, the following nine types of sets are conceivable: Ev={Im: Sm1, In: Sn1}, Ev={Im: Sm1, In: Sn2}, Ev={Im: Sm1}, Ev={Im: Sm2, In: Sn1}, Ev={Im: Sm2, In: Sn2}, Ev={Im: Sm2}, Ev={In: Sn1}, Ev={In: Sn2}, and Ev=ϕ.

In addition, each subset of Ef will be written as Efp (p=1, 2, . . . ) hereinafter. Furthermore, Ev which can be obtained from Nv is written as Evq (q=1, 2, . . . ). Efp and Evq correspond to reference information candidates described above.

In step S3000, the input information obtaining unit 102 obtains information input to the diagnosis support apparatus 100 as input information. Assume that in this embodiment, input information includes a medical image, representative image, clinical information, and the coordinate information of an abnormal shadow.

In step S3010, the image feature obtaining unit 104 obtains an image feature amount from the medical image obtained in step S3000 by processing the image. The image feature amount obtained in this case may be a general image feature amount such as the average or variance of densities (luminances) of the entire image, or an image feature amount specialized for the derivation of a specific imaging finding.

In this embodiment, the image feature obtaining unit 104 performs image processing for a region obtained based on coordinate information included in the input information. That is, the image feature obtaining unit 104 performs image processing for an abnormal shadow region extracted by using a known segmentation technique while referring to the coordinate information of the abnormal shadow obtained in step S3000. An example of an image feature amount obtained in this embodiment will be described, together with a description of step S3020.

In step S3020, the imaging finding deriving unit 106 derives an imaging finding by using the image feature amount obtained in step S3010.

Figure 5:
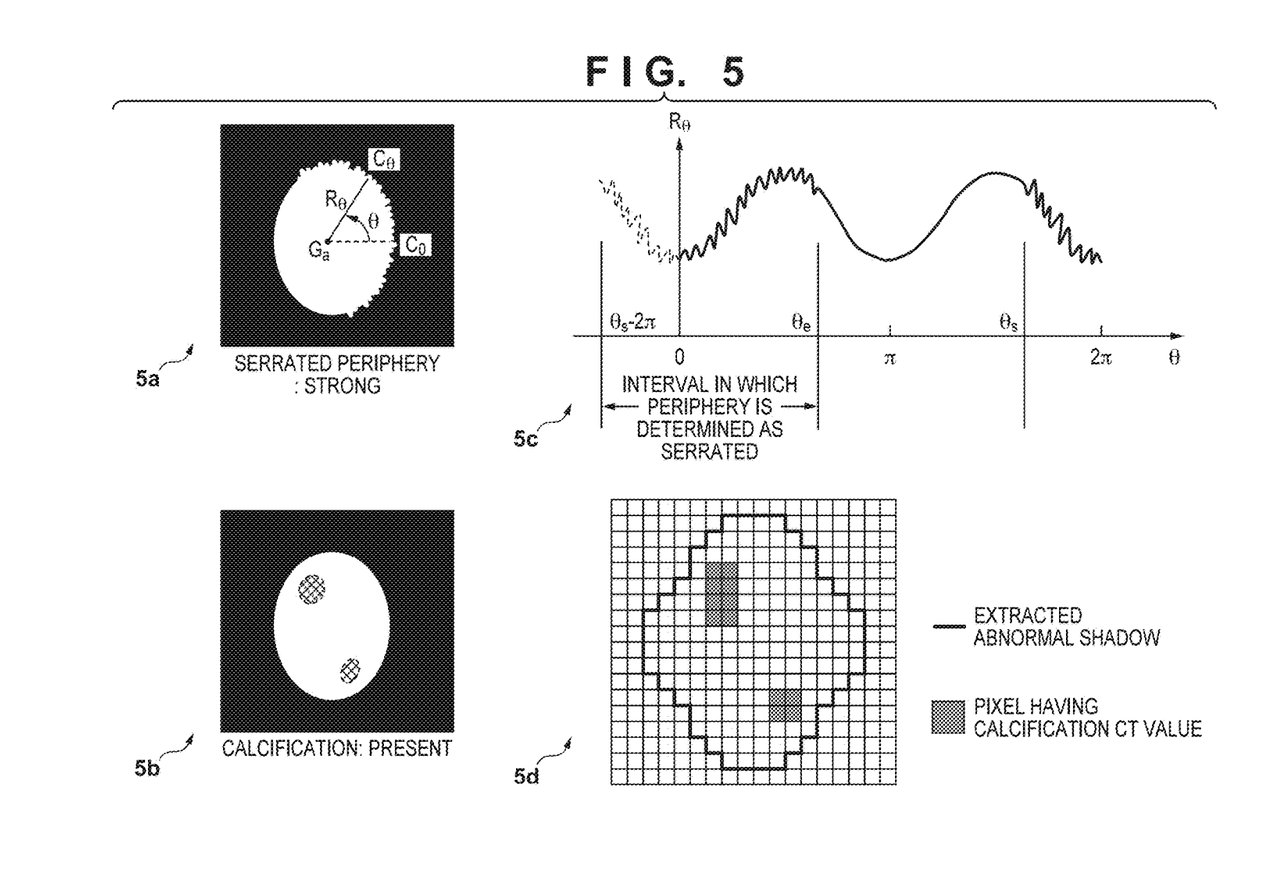
FIG. 5 shows an example of deriving imaging findings by using image feature amounts.

FIG. 5 shows an example of deriving an imaging finding by using an image feature amount. For example, with regard to an imaging finding "serrated periphery" (I3) (5a and 5c in FIG. 5), in step S3010, after the extraction of an abnormal shadow region, the imaging finding deriving unit 106 selects a slice, of slices (axial slices) perpendicular to the craniocaudal direction of the abnormal shadow region, on which the longitudinal diameter of the abnormal shadow region becomes the maximum. The imaging finding deriving unit 106 then obtains a gravity center Ga (the average position of all the pixels in an abnormal shadow region on the slice) on the axial slice. In addition, the imaging finding deriving unit 106 sets a half line extending from the gravity center Ga at a counterclockwise angle θ with reference to a horizontal right direction from the gravity center Ga. The imaging finding deriving unit 106 obtains distances Rθ between Ga and points (Cθ) at which the half line intersects with the boundary line of the abnormal shadow region at given angular intervals (for example, π/180). Thereafter, the imaging finding deriving unit 106 generates a graph, with the abscissa representing an angle θ and the ordinate representing a distance Rθ, and obtains high-frequency components by using Fourier transform/inverse transform. If an angle interval in which high-frequency components are continuously detected exceeds a given threshold (for example, π/18), the imaging finding deriving unit 106 determines that the angle interval is a portion whose periphery is serrated.

Note that the angles between θ=0 and θ=2π are regarded as continuous. Consider, for example, a case in which high-frequency components are continuous from θ=0 to θ=θe, and high-frequency components are continuous from θ=θs to θ=2π. In this case, regarding that high-frequency components are continuous from (θs 0 2π) to θe, the imaging finding deriving unit 106 determines whether the angle interval is equal to or more than a threshold. The imaging finding deriving unit 106 then decides the strength of a serrated periphery in accordance with the ratio of the angle interval determined as the serrated periphery to the entire circumference (2π). If, for example, the ratio of a given interval indicating a serrated periphery is 50% or more, the imaging finding deriving unit 106 decides the interval as "serrated periphery: strong". Note that if a plurality of peripheries indicating serrated peripheries exist separately from each other, the imaging finding deriving unit 106 can perform calculation by using the sum of the respective angle intervals.

With regard to the imaging finding "calcification" (5b and 5d in FIG. 5), the imaging finding deriving unit 106 can derive an imaging finding by obtaining the ratio of pixels having calcification densities (in the case of CT, for example, a CT value of 200 HU or more) to the total pixels in an extracted abnormal shadow region. In this case, in consideration of noise, if, for example, four or more such pixels are not continuous, the corresponding densities may not be counted as calcification densities. If, for example, the ratio of pixels having calcification densities exceeds 10%, "calcification: present" may be determined.

In the following description, a set including, as elements, items corresponding to derived imaging findings (to be referred to as derived findings hereinafter) is written as Nd, and a set including, as elements, pairs of the respective items of Nd and their states is written as Ed. Assume that the imaging finding deriving unit 106 has derived, as derived findings, item I1 "shape": state S12 "lobular", item I2 "notch": state S22 "strong", . . . , and item I1 "involvement (bronchus)": state S11 "present". In this case, Nd and Ed are respectively given as Nd={I1, I2, . . . , I1} and Ed={S12, S21, . . . , S11}.

In step S3030, the inference unit 108 executes inference concerning an abnormal shadow in the lung as a diagnosis target based on the input information (imaging finding and/or clinical information) obtained in step S3000 and the derived finding derived in step S3020. As a method of performing inference (inference method) at this time, it is possible to use one of various existing methods such as a Bayesian network, neural network, and support vector machine. This embodiment uses the Bayesian network as an inference method executed by the inference unit 108. The Bayesian network is an inference model using conditional probabilities. It is possible to obtain the inference probability of each diagnosis name when information is input (the probability of the case being each diagnosis name; also called a posterior probability). In this embodiment, the inference unit 108 obtains the inference probabilities of diagnosis names D1, D2, and D3 of abnormal shadows. Note that in this embodiment, the inference unit 108 executes inference by using an evidence (information to be used to obtain an inference result) as described above. That is, the inference unit 108 obtains P(Dd|Ef).

More specifically, letting Ni be a set including, as elements, items of input information (imaging findings and/or clinical information) obtained in step S3000 and Ei be a set including, as elements, pairs of the respective items of Ni and their states, the inference unit 108 executes an inference by calculating the union of Nd and Ed as an evidence (Nf, Ef). Note that for the sake of simplicity, assume that Ni and Nd include no common items. That is, Ei and Ed have no contradictory states (for example, S11 and S12). Assume that imaging findings and/or clinical information of the input information obtained in step S3000 include item Im "CEA": state Sm2 "abnormal value", . . . , item In "history": state Sn2 "absent". In this case, Ni and Ei are respectively given as Ni={Im, . . . , In} and Ei={Sm2, . . . , Sn2}. In addition, if Nd and Ed are those described above in the above example, the union Nf of Ni and Nd and the union Ef of Ei and Ed are respectively given as Nf={I1, I2, . . . , I1, . . . , In} and Ef={S12, S21, . . . , S11, . . . , Sn2}.

In step S3040, the inference unit 108 obtains the influence degrees of evidence information with respect to the inference probabilities as the influence degrees of the inference information candidates by using the inference probabilities and the evidence information used to obtain the inference results. That is, the inference unit 108 obtains the influence degrees of the reference information candidates with respect to the inference results by using the inference probabilities (inference results) obtained in step S3030 and the information used to obtain the inference results. In this embodiment, reference information candidates are defined as subsets Efp of Ef.

For example, in order to obtain the subsets Efp each having an element count of 2 from Ef={S12, S21, . . . , S11, . . . , Sn2}, Efp such as {S12, S21}, {S12, S11}, and {S21, Sn2} are obtained. Assume that in this embodiment, all subsets Efp each having an element count of 1 are obtained. If Ef includes t elements, t subsets Efp are obtained.

The inference unit 108 then obtains the influence degree of an inference result with respect to each subset Efp. In this embodiment, the inference unit 108 obtains an influence degree I(Df|Efp) of Efp with respect to a diagnosis name Df exhibiting the highest probability among the inference probabilities of the respective diagnosis names obtained in step S3030. In addition, in the embodiment, an influence degree is defined by equation (1) given below:

$$I(Df|Efp) = P(Df|Ef) - P(Df|Ef-Efp) \qquad (1)$$

In equation (1) given above, a change in the posterior probability of the diagnosis name Df obtained by subtracting Efp from Ef is the influence degree of Efp. If this value is positive, it indicates that the posterior probability of Df decreases when Efp is subtracted from Ef. Therefore, it can be said that Efp is information supporting Df.

In step S3050, the selection unit 110 selects reference information from the reference information candidates based on the inference probabilities and the influence degrees of the reference information candidates obtained by the inference unit 108. That is, the selection unit 110 selects reference information (information as a clue for diagnosis) from the reference information candidates by using the inference probabilities (inference results) obtained in step S3030 and the influence degrees of the reference information candidates obtained in step S3040. In this embodiment, the selection unit 110 selects a plurality of subsets Efp as reference information in descending order of influence degrees.

In step S3060, the partial region specifying unit 112 specifies a partial region of the medical image based on the image feature amounts obtained in step S3010 and the reference information selected in step S3050. More specifically, the partial region specifying unit 112 specifies a partial region based on the image feature amounts corresponding to the reference information when the reference information can be associated with the image feature amounts. If they cannot be associated with each other, for example, an upper portion of the image is specified as a partial region. Alternatively, it is possible to perform processing while regarding that there is no partial region.

Figure 6A:
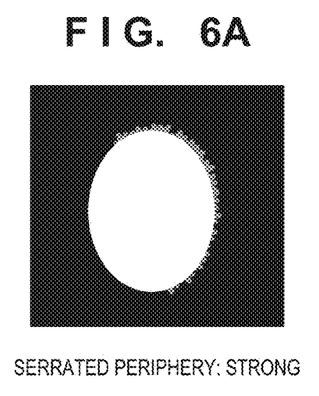
FIGS. 6A to 6D are views showing an example of specifying a partial region.
Figure 6B:
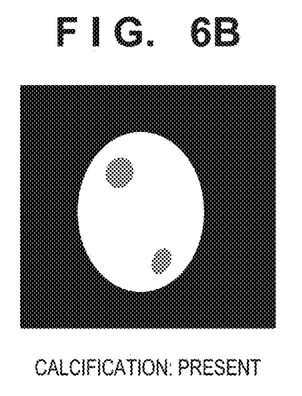
Figure 6C:
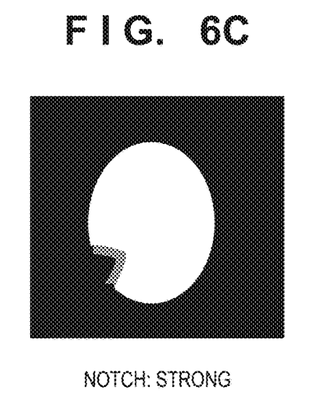
Figure 6D:
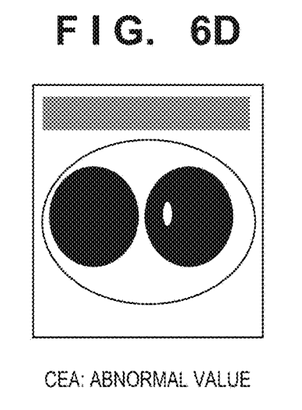

FIGS. 6A to 6D are views each showing an example of specifying a partial region. The partial region specifying unit 112 can specify, as a partial region, a region having an image feature corresponding to reference information. Referring to FIG. 6A, the partial region specifying unit 112 specifies, as a partial region, a portion determined as a serrated portion of a periphery of an abnormal shadow based on the reference information "serrated periphery: strong". Likewise, referring to FIG. 6B, the partial region specifying unit 112 specifies, as a partial region, a pixel having a calcification density in the abnormal shadow based on the reference information "calcification: present". Referring to FIG. 6C, the partial region specifying unit 112 specifies, as a partial region, a portion determined as a notch on the periphery of the abnormal shadow based on the reference information "notch: strong". Note that when determining a periphery having a notch, it is possible to use the technique disclosed in, for example, Japanese Patent Laid-Open No. 2011-131022. Referring to FIG. 6D, since reference information is "CEA: abnormal value" and does not correspond to an image feature amount, an upper portion of the image is specified as a partial region. Note that, referring to FIG. 6D, a partial region to be specified is not limited to the upper portion of the image, and it is possible to specify a portion of an empty region of the image.

In step S3070, the display control unit 114 controls information to be displayed on the monitor based on the information input to the display control unit 114. The display control unit 114 displays information for identifying the specified partial region on or in the vicinity of the partial region. More specifically, the display control unit 114 controls the monitor to change display with respect to the partial region specified in step S3060. Assume that in this embodiment, when the reference information can be associated with the image feature amount, the display control unit 114 adds, to the specified partial region, identification information (marker) for identifying the partial region in the medical image. For example, the identification information (marker) can be added to the specified partial region by superimposing/displaying a layer on only the partial region so as to superimpose a color (for example, translucent red). In contrast to this, if the reference information does not correspond to the image feature amount, character information based on the reference information (for example, the measurement value of a tumor marker if the reference information is the tumor marker) is displayed on the specified partial region. Note that the change of display described above is an example, and this embodiment is not limited to this example. Another example of changing display by the display control unit 114 will be described later in the fourth modification.

Figure 7:
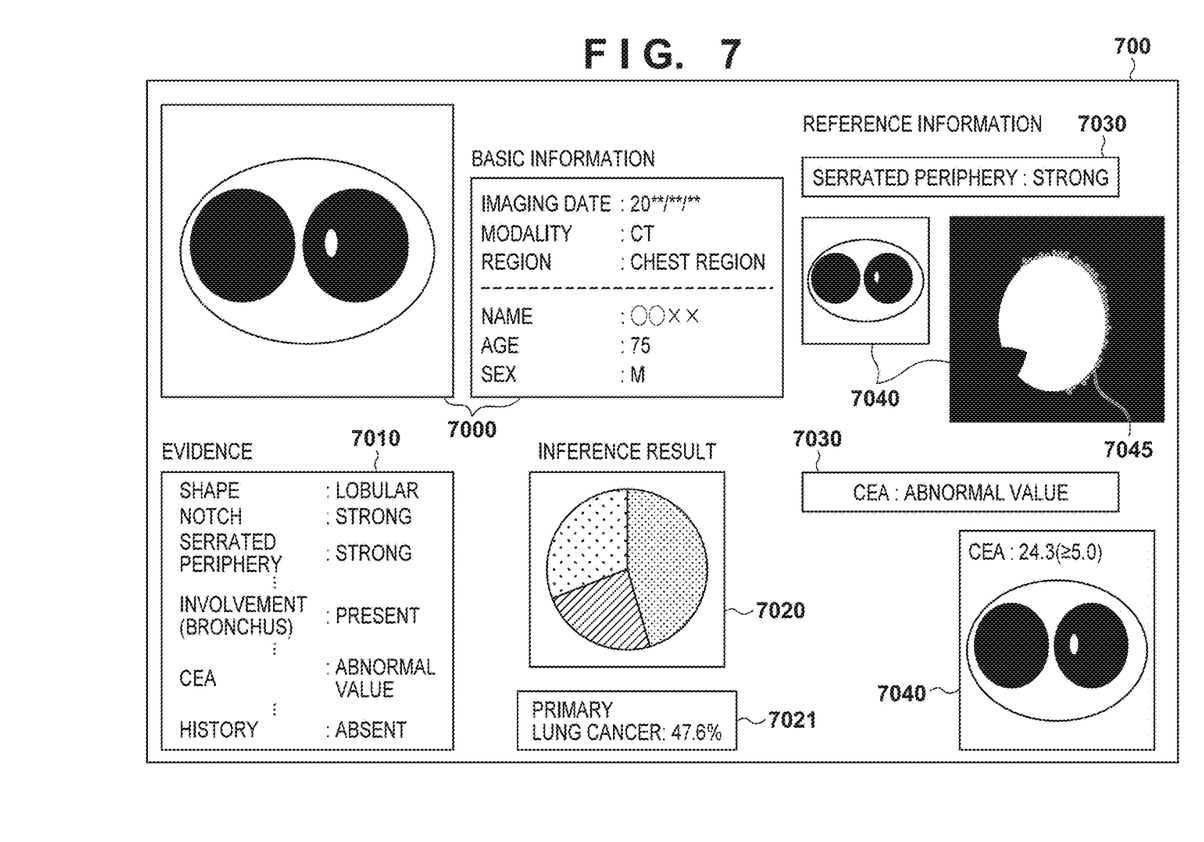
FIG. 7 is a view showing an example of information displayed on a monitor.

FIG. 7 is a view exemplarily showing information displayed on the monitor by the display control unit 114 in step S3070. Information 700 to be displayed on the monitor includes basic information 7000, an evidence 7010, an inference result 7020-7021, reference information 7030, and an image 7040 having undergone a change in the display of a partial region. The display control unit 114 can display the reference information and the partial region having undergone display control in combination with each other. The display control unit 114 can also display the reference information, the partial region having undergone display control, and the inference result in combination with each other.

The basic information 7000 indicates basic information such as the imaging date of the image, the type of modality which has obtained the image, and the age, sex, and the like of the patient by using the information obtained in step S3000. The image 7040 having undergone the change in the display of the partial region is obtained by superimposing/displaying a layer on the medical image so as to add a marker 7045 to the image.

The user (doctor) can use the inference result 7020-7021 and the image 7040 having undergone the change in the display of the partial region (and the reference information 7030) as diagnosis support information for radiogram interpretation by himself/herself. When the reference information 7030 corresponds to the image feature amount, in particular, the doctor can quickly check the specific position of the reference information 7030 on the image by seeing the image 7040 having undergone the change in the display of the partial region, and hence can easily comprehend diagnosis support information.

According to this embodiment, it is possible to reduce time and effort taken by the user to comprehend reference information by presenting the reference information on an image browsed by the user. That is, the diagnosis support apparatus 100 can identify reference information as a clue for diagnosis based on input information concerning a medical image and present a partial region indicated by the reference information on the medical image. This allows the user (doctor) to easily check the reference information on the medical image. This makes it possible to reduce the load on the user (doctor) when comprehending the reference information.

Second Embodiment

The first embodiment described above is configured to obtain a medical image and clinical information as input information, identify reference information from the input information, and present the information on the medical image. A diagnosis support apparatus 100 according to the second embodiment obtains an imaging finding input by the user in addition to a medical image and clinical information, identifies reference information from the input imaging finding and medical information other than the clinical information, and presents the information on the medical image. Note that the functional arrangement of the diagnosis support apparatus 100 according to this embodiment is the same as that shown in FIG. 1 in the first embodiment. In addition, the hardware arrangement of the diagnosis support apparatus 100 is the same as that shown in FIG. 2 in the first embodiment. That is, a CPU 1001 executes programs stored in a main memory 1002 and a magnetic disk 1003 to implement the functions (software) of the diagnosis support apparatus 100 according to the embodiment and the processing in the flowchart.

The flowchart for explaining overall processing performed by the diagnosis support apparatus 100 is the same as that shown in FIG. 3. However, this processing is partly different from that in the first embodiment. Only differences in the overall processing performed by the diagnosis support apparatus 100 according to this embodiment from the first embodiment will be described below with reference to the flowchart of FIG. 3.

In step S3000, an input information obtaining unit 102 obtains information input to the diagnosis support apparatus 100 as input information. Assume that in this embodiment, input information includes a medical image, representative image, clinical information, the coordinate information of an abnormal shadow, and an imaging finding about the abnormal shadow input by the user via a case information terminal 200.

Processing in steps S3010 and S3020 is the same as that in the first embodiment. That is, in step S3010, an image feature obtaining unit 104 obtains an image feature (image feature amount) from the medical image obtained in step S3000 by processing the medical image. In step S3020, an imaging finding deriving unit 106 derives an imaging finding by using the image feature amount obtained in step S3010.

In step S3030, an inference unit 108 executes inference concerning the abnormal shadow in the lung as a diagnosis target based on the input information (imaging finding and/or clinical information) obtained in step S3000. That is, in this embodiment, evidences (information used to obtain an inference result) Nf and Ef respectively coincide with a set Ni including, as elements, items of input information (imaging findings and/or clinical information) and a set Ei including, as elements, pairs of the respective items of Ni and their states. The inference unit 108 executes inference by using evidences (information used to obtain an inference result). That is, the inference unit 108 obtains P(Dd|Ef) as in the first embodiment.

In step S3040, the inference unit 108 obtains the influence degree of a reference information candidate corresponding to the inference result by using the inference probability (inference result) obtained in step S3030. In this embodiment, reference information candidates are defined as Evq (including one element) which can be obtained from non-input information Nv. Assume, however, that only some of Evq are left and their influence degrees are calculated based on the set Nd including, as elements, the items of imaging findings (derived findings) derived in step S3020 and the set Ed including, as elements, pairs of the respective items of Nd and their states.

More specifically, the inference unit 108 obtains, as reference information candidates, Evq having elements of Ed which have states of Nd concerning items common to Nv and Nd (that is, Nv∩Nd). If, for example, Nv∩Nd={I2, I4} and Ed={S12, S21, S31, S42, . . . , S11}, the inference unit 108 obtains, as reference information candidates, Evq={S21} indicating the state of the item I2 and Evq={S42} indicating the state of the item I4. That is, this indicates that non-input information which can decide the state of a given item based on a derived finding is left as a reference information candidate.

In addition, the inference unit 108 obtains, as reference information candidates, all Evq which can be obtained from items which are included in Nv but are not included in Nd (that is, Nv\Nd). For example, if Nv\Nd={In}, the inference unit 108 obtains, as reference information candidates, Evq={Sn1} and Evq={Sn2} which indicate the state of the item In. The inference unit 108 obtains, as reference information candidates, non-input information, of input information obtained by the input information obtaining unit 102, which has not been input to the inference unit 108. This indicates that all pieces of information, of non-input information, whose states cannot be decided based on derived findings, are left as reference information candidates.

The inference unit 108 then obtains a change in inference probability when evidence information (Ef) is added to non-input information (Evq) as the influence degree of a reference information candidate corresponding to the non-input information. That is, the inference unit 108 obtains the influence degree of the obtained reference information candidate Evq on the inference result. In this embodiment, the inference unit 108 obtains an influence degree I(Df|Evq) of the non-input information Evq corresponding to the diagnosis name Df, of the respective diagnosis names obtained in step S3030, which exhibits the highest inference probability. In the embodiment, an influence degree is defined by equation (2) given below:

$$I(Df|Evq)=P(Df|Ef\cup Evq)-P(Df|Ef) \qquad (2)$$

According to equation (2) given above, a change in the posterior probability of the diagnosis name Df when Evq is added to Ef is set as the influence degree of Evq. If this value is positive, it indicates that the posterior probability of Df increases as Evq is added to Ef, it can be said that Evq is information supporting Df.

In step S3050, a selection unit 110 selects pieces of reference information (pieces of information as clues for diagnosis) based on the inference results obtained in step S3030 and the influence degrees of the reference information candidates obtained in step S3040. In this embodiment, the selection unit 110 selects a plurality of subsets Evp as reference information in descending order of influence degrees.

Processing in steps S3060 and S3070 is the same as that in the first embodiment. That is, in step S3060, a partial region specifying unit 112 specifies a partial region of the medical image based on the image feature amounts obtained in step S3010 and the reference information selected in step S3050. In step S3070, a display control unit 114 controls information to be displayed on the monitor based on the information input to the display control unit 114.

According to this embodiment, the diagnosis support apparatus 100 identifies reference information as a clue for diagnosis from clinical information which has not been input by the user and imaging findings which have not been input by the system based on input information concerning a medical image. Presenting a partial region designated by the reference information on the medical image allows the user to easily check reference information which has not been input by the doctor/system on the medical image. This can present reference information which has not been considered by the doctor and reduce the load on the user in comprehending reference information.

First Modification

In the first embodiment, the diagnosis support apparatus 100 does not obtain any imaging finding input by the user. However, the first embodiment may be configured to obtain imaging findings input by the user. In this case, when the inference unit 108 generates an evidence in step S3030, an imaging finding input by the user may differ from a derived finding derived in step S3020 in the state of the same item. In this case, the inference unit 108 may give priority to either the state of the imaging finding input by the user or the state of the derived finding. The inference unit 108 may also has an arrangement configured to display the states of the two types of findings and make the user select one of them.

Second Modification

In the two embodiments described above, an image feature amount is obtained in step S3010, and an imaging finding is derived based on the obtained image feature amount in step S3020, thereby generating a reference information candidate by using the derived imaging finding. However, the arrangement of each embodiment is not limited to this example, and processing need not always be performed in this order. For example, after a reference information candidate is generated based on input information and reference information is decided, an image feature amount concerning the reference information may be obtained. In this case, when generating a reference information candidate from an evidence like that described in the first embodiment, an imaging finding input by the user may be obtained.

Third Modification

In the two embodiments described above, in step S3050, the selection unit 110 selects reference information based on inference results obtained by the inference unit 108 in step S3030 and influence degrees obtained in step S3040. However, the arrangement of each embodiment is not limited to this example, and it is not always necessary to use inference results and influence degrees. The selection unit 110 can select reference information as a clue for medical diagnosis from reference information candidates generated by using medical information. For example, the selection unit 110 may arbitrarily select reference information from all reference information candidates. In this case, the selection unit 110 may be an arrangement configured to display all the reference information candidates and make the user select candidates from the displayed candidates. In this case, the image feature obtaining unit 104 obtains image features corresponding to reference information from the medical image. The partial region specifying unit 112 then specifies a partial region of the medical image based on the reference information and the image features. In addition, the display control unit 114 can control the display of the medical image based on the selected reference information and the partial region.

The display control unit 114 performs display control to, for example, enable the monitor to emphasize and display a partial region, of a medical image, which is specified based on reference information and an image feature, or a portion in the vicinity of the partial region. In addition, the display control unit 114 performs display control to, for example, enable the monitor to display identification information for identifying a specified partial region on or in the vicinity of the partial region. Furthermore, the display control unit 114 enables the monitor to change a display attribute of a specified partial region or a portion in the vicinity of the partial region. The display control unit 114 can control display of a region having an image feature corresponding to reference information as a partial region.

Fourth Modification

Figure 8A:
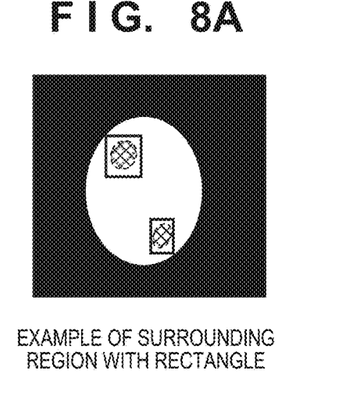
FIGS. 8A and 8B are views each showing another example of changing display of a specified partial region.
Figure 8B:
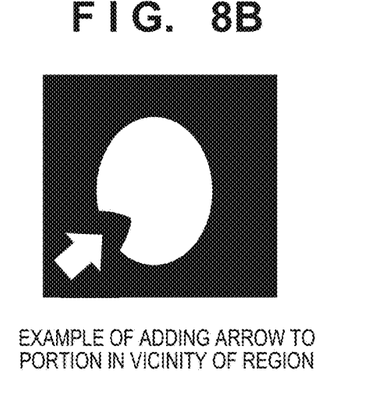

In the two embodiments, in step S3070, identification information (marker) for identifying a partial region is added to a specified partial region by superimposing and displaying a layer on the partial region so as to superimpose a color only on it. However, the arrangement of each embodiment is not limited to this example. For example, the display control unit 114 may surround a specified partial region with a graphic pattern (for example, a circular or rectangular pattern) having a predetermined shape (FIG. 8A). Alternatively, the display control unit 114 may add identification information (marker) for identifying a partial region to a specified partial region by adding a graphic pattern such as an arrow to a portion in the vicinity of the partial region (FIG. 8B). That is, any type of identification information (marker) can be used as long as a display form to be used allows easy visual recognition of a specified partial region.

Alternatively, the display control unit 114 can change a display attribute of a partial region or a display attribute of a portion in the vicinity of the partial region. The display control unit 114 can change the pixel value of a partial region specified in a medical image. For example, when a medical image is a gray-scale image, the display control unit 114 can change the image into a color image and change a pixel value so as to allow easy visual recognition of a specified partial region.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-099513, filed May 14, 2015, which is hereby incorporated by reference herein in its entirety.

What is claimed is:

1. A diagnosis support apparatus which provides information for supporting medical diagnosis, the apparatus comprising:
   a selection unit configured to select an imaging finding as a clue for medical diagnosis from candidates of the imaging finding generated by using medical information;
   an obtaining unit configured to obtain an image feature corresponding to the selected imaging finding from a medical image;
   a specifying unit configured to specify a portion in an abnormal shadow on the basis of the image feature, the portion being a partial region indicated by the selected imaging finding; and
   a display control unit configured to display, on a display unit, the specified portion in the abnormal shadow included in the medical image together with a remaining region included in the medical image by displaying the medical image, wherein
   the display control unit is configured to display, on the display unit, the specified portion in the abnormal shadow or a portion in the vicinity of the specified portion in the abnormal shadow so as to emphasize the specified portion in the abnormal shadow or the portion in the vicinity of the specified portion in the abnormal shadow compared to the displayed remaining region.

2. The apparatus according to claim 1, wherein the display control unit is configured to display identification information for identifying the specified portion in the abnormal shadow on or in the vicinity of the portion in the abnormal shadow.

3. The apparatus according to claim 1, wherein the display control unit is configured to change a display attribute of the specified portion in the abnormal shadow or a display attribute of the portion in the vicinity of the portion in the abnormal shadow.

4. The apparatus according to claim 1, wherein the display control unit is configured to control the display of a region having the image feature corresponding to the imaging finding as the portion in the abnormal shadow.

5. The apparatus according to claim 1, wherein the display control unit is configured to display information on the imaging finding and the portion in the abnormal shadow having undergone control of the display in combination with each other.

6. The apparatus according to claim 1, wherein the specifying unit is configured to specify, as the portion in the abnormal shadow, a region having the image feature corresponding to the imaging finding.

7. The apparatus according to claim 1, wherein the obtaining unit is configured to obtain an image feature of a medical image as a diagnosis target by performing image processing for the medical image based on input information obtained by the input information obtaining unit.

8. The apparatus according to claim 7, wherein the obtaining unit is configured to perform the image processing for a region obtained based on coordinate information included in the input information.

9. The apparatus according to claim 1, further comprising a deriving unit configured to derive an imaging finding based on an image feature obtained by the obtaining unit, wherein
   the deriving unit is configured to derive an imaging finding as a diagnosis target from a comparison result on the image feature and a threshold.

10. The apparatus according to claim 9, further comprising an inference unit configured to execute inference for obtaining a diagnosis name corresponding to the diagnosis target and an inference probability corresponding to the diagnosis name based on input information obtained by the input information obtaining unit and the imaging finding derived by the deriving unit.

11. The apparatus according to claim 10, wherein the inference unit is configured to obtain the inference probability with respect to each of a plurality of diagnosis names as a result of the inference.

12. The apparatus according to claim 10, wherein the inference unit is configured to obtain an influence degree of evidence information used to obtain a result of the inference with respect to the inference probability as an influence degree of the candidate by using the inference probability and the evidence information.

13. The apparatus according to claim 12, wherein the inference unit is configured to obtain, as the candidate, non-input information, of input information obtained by the input information obtaining unit, which has not been input to the inference unit.

14. The apparatus according to claim 13, wherein the inference unit is configured to obtain a change in the inference probability in a case where the non-input information is added to the evidence information as an influence degree of the candidate corresponding to the non-input information.

15. The apparatus according to claim 12, wherein the selection unit is configured to select, based on the inference probability and influence degrees of the candidates which are obtained by the inference unit, an imaging finding from the candidates.

16. The apparatus according to claim 10, wherein the display control unit is configured to display information on the imaging finding, the portion in the abnormal shadow having undergone control of the display, and a result of the inference in combination with each other.

17. An information processing method for providing information for supporting medical diagnosis, the method comprising:

selecting an imaging finding as a clue for medical diagnosis from candidates of the imaging finding generated by using medical information;

obtaining an image feature corresponding to the selecting imaging finding from a medical image;

specifying a portion in an abnormal shadow on the basis of the image feature, the portion being a partial region indicated by the selected imaging finding; and displaying, on a display unit, the specified portion in the abnormal shadow included in the medical image together with a remaining region included in the medical image by displaying the medical image, wherein the displaying includes displaying, on the display unit, the specified portion in the abnormal shadow or a portion in the vicinity of the specified portion in the abnormal shadow so as to emphasize the specified portion in the abnormal shadow or the portion in the vicinity of the specified portion in the abnormal shadow compared to the displayed remaining region.

18. A non-transitory computer-readable storage medium storing a program for causing a computer to function as each unit of a diagnosis support apparatus, the diagnosis support apparatus comprising:

a selection unit configured to select an imaging finding as a clue for medical diagnosis from candidates of the imaging finding generated by using medical information;

an obtaining unit configured to obtain an image feature corresponding to the selected imaging finding from a medical image;

a specifying unit configured to specify a portion in an abnormal shadow on the basis of the image feature, the portion being a partial region indicated by the selected imaging finding; and a display control unit configured to display, on a display unit, the specified portion in the abnormal shadow included in the medical image together with a remaining region included in the medical image by displaying the medical image, wherein the display control unit is configured to control display, on the display unit, the specified portion in the abnormal shadow or a portion in the vicinity of the specified portion in the abnormal shadow so as to emphasize the specified portion in the abnormal shadow or the portion in the vicinity of the specified portion in the abnormal shadow compared to the displayed remaining region.

19. A diagnosis support apparatus which provides information for supporting medical diagnosis, the apparatus comprising a processor and a memory, the processor and the memory being operatively coupled to function as:

a selection unit configured to select an imaging finding as a clue for medical diagnosis from candidates of the imaging finding generated by using medical information;

an obtaining unit configured to obtain an image feature corresponding to the selected imaging finding from a medical image;

a specifying unit configured to specify a portion in an abnormal shadow on the basis of the image feature, the portion being a partial region indicated by the selected imaging finding; and a display control unit configured to display, on a display unit, the specified portion in the abnormal shadow included in the medical image together with a remaining region included in the medical image by displaying the medical image, wherein the display control unit is configured to display, on the display unit, the specified portion in the abnormal shadow or a portion in the vicinity of the specified portion in the abnormal shadow so as to emphasize the specified portion in the abnormal shadow or the portion in the vicinity of the specified portion in the abnormal shadow compared to the displayed remaining region.

* * * * *